United States Patent
Joshi

(10) Patent No.: US 7,349,733 B2
(45) Date of Patent: Mar. 25, 2008

(54) IONTOPHORETIC DRUG DELIVERY SYSTEMS

(75) Inventor: Ashok V. Joshi, Salt Lake City, UT (US)

(73) Assignee: Ceramatel, Inc., Salt Lake City, UT (US)

( * ) Notice: Subject to any disclaimer, the term of this patent is extended or adjusted under 35 U.S.C. 154(b) by 0 days.

(21) Appl. No.: 10/003,853

(22) Filed: Nov. 2, 2001

(65) Prior Publication Data

US 2003/0088204 A1 May 8, 2003

(51) Int. Cl.
*A61N 1/30* (2006.01)

(52) U.S. Cl. ...................................... 604/20

(58) Field of Classification Search .................. 604/20, 604/501, 21, 22, 500, 19, 890.1, 891.1, 892.1; 600/377
See application file for complete search history.

(56) References Cited

U.S. PATENT DOCUMENTS

| | | | |
|---|---|---|---|
| 3,604,417 A | 9/1971 | Stolzenberg et al. | |
| 3,760,805 A | 9/1973 | Higuchi | |
| 3,760,984 A | 9/1973 | Theeuwes | |
| 3,773,919 A | 11/1973 | Boswell et al. | |
| 3,797,494 A | 3/1974 | Zaffaroni | |
| 3,995,631 A | 12/1976 | Higuchi et al. | |
| 4,003,379 A | 1/1977 | Ellinwood, Jr. | |
| 4,034,756 A | 7/1977 | Higuchi et al. | |
| 4,140,122 A * | 2/1979 | Kuhl et al. | 604/20 |
| 4,141,359 A | 2/1979 | Jacobsen et al. | |
| 4,240,884 A | 12/1980 | Pellegri | |
| 4,250,878 A | 2/1981 | Jacobsen et al. | |
| 4,292,968 A | 10/1981 | Ellis | |
| 4,452,249 A | 6/1984 | Sachs et al. | |
| 4,474,570 A | 10/1984 | Ariura et al. | |
| 4,522,698 A | 6/1985 | Maget | |
| 4,539,004 A | 9/1985 | Eckenhoff et al. | |
| 4,557,723 A | 12/1985 | Sibalis | |
| 4,744,787 A | 5/1988 | Phipps et al. | |
| 4,752,285 A | 6/1988 | Petelenz et al. | |
| 4,820,263 A | 4/1989 | Spevak et al. | |
| 4,886,489 A | 12/1989 | Jacobsen et al. | |
| 4,886,514 A | 12/1989 | Maget | |
| 4,927,408 A | 5/1990 | Haak et al. | |

(Continued)

FOREIGN PATENT DOCUMENTS

EP 0 931 564 A1 7/1999

OTHER PUBLICATIONS

"Transdermal patch", *Wikipedia*, http://en.wikipedia.org/wiki/Transdermal_patch. Retrieved Feb. 12, 2007, 1-2.

(Continued)

*Primary Examiner*—Matthew F. DeSanto

(57) ABSTRACT

An electrotransport device is provided for the site specific delivery of drugs or other beneficial agents across or under a skin or tissue surface. In one embodiment, the electrotransport device is configured in whole, or in part, to be implanted under a subject's stratum corneum, and uses an electrical current to facilitate drug or other beneficial agent delivery through a semipermeable membrane and into the tissue of the subject. In another embodiment, a device for intraocular delivery of drug or beneficial agent is disclosed which device is placed on the conjunctiva of a subject, wherein lacrimal fluid completes a circuit for delivering the drug or beneficial agent. Methods of using the devices of the present invention are also provided.

38 Claims, 4 Drawing Sheets

U.S. PATENT DOCUMENTS

| | | | |
|---|---|---|---|
| 4,929,233 A | | 5/1990 | Roth et al. |
| 4,973,303 A | | 11/1990 | Johnson et al. |
| 5,035,711 A | | 7/1991 | Aoki et al. |
| 5,041,107 A | | 8/1991 | Heil, Jr. |
| 5,063,175 A | | 11/1991 | Broadbent et al. |
| 5,125,894 A | | 6/1992 | Phipps et al. |
| 5,250,023 A | | 10/1993 | Lee et al. |
| 5,286,254 A | | 2/1994 | Shapland et al. |
| 5,413,572 A | | 5/1995 | Wong et al. |
| 5,427,870 A | | 6/1995 | Joshi et al. |
| 5,445,606 A | * | 8/1995 | Haak et al. ............ 604/20 |
| 5,454,922 A | | 10/1995 | Joshi et al. |
| 5,492,534 A | | 2/1996 | Athayde et al. |
| 5,618,265 A | * | 4/1997 | Myers et al. ............ 604/20 |
| 5,647,844 A | | 7/1997 | Haak et al. |
| 5,672,167 A | | 9/1997 | Athayde et al. |
| 5,700,481 A | | 12/1997 | Iga et al. |
| 5,735,897 A | | 4/1998 | Buirge |
| 5,857,992 A | * | 1/1999 | Haak et al. ............ 604/521 |
| 5,869,078 A | | 2/1999 | Baudino |
| 5,876,741 A | | 3/1999 | Ron |
| 5,911,223 A | | 6/1999 | Weaver et al. |
| 5,954,268 A | | 9/1999 | Joshi et al. |
| 5,971,722 A | | 10/1999 | Maget et al. |
| 5,983,130 A | | 11/1999 | Phipps et al. |
| 6,001,088 A | * | 12/1999 | Roberts et al. ............ 604/501 |
| 6,261,595 B1 | | 7/2001 | Stanley et al. |
| 6,421,561 B1 | | 7/2002 | Morris et al. |
| 6,505,069 B2 | | 1/2003 | Scott et al. |
| 6,535,761 B2 | | 3/2003 | Bernabei |
| 6,584,349 B1 | * | 6/2003 | Sage et al. ............ 604/20 |
| 6,591,133 B1 | | 7/2003 | Joshi |
| 6,615,079 B1 | * | 9/2003 | Avrahami ............ 604/20 |
| 6,662,044 B2 | | 12/2003 | Crawford et al. |
| 6,748,266 B2 | | 6/2004 | Bernabei |
| 7,031,768 B2 | * | 4/2006 | Anderson et al. ............ 604/20 |
| 7,083,580 B2 | | 8/2006 | Bernabei |
| 2002/0099358 A1 | * | 7/2002 | Llyod et al. ............ 604/890.1 |

OTHER PUBLICATIONS

Bockelman, Office Action for U.S. Appl. No. 09/674,211, filed Mar. 14, 2001, 1-9.

Bockelman, Office Action for U.S. Appl. No. 09/674,211, filed Sep. 27, 2001, 1-6.

Bockelman, Office Action for U.S. Appl. No. 09/674,211, filed Feb. 12, 2002, 1-6.

Mersereau, C. G., SIDS for U.S. Appl. No. 09/674,211, filed Jan. 30, 2001, 1-4.

Mersereau, C. G., IDS for U.S. Appl. No. 09/674,211, filed Jan. 30, 2001, 1-5.

Mersereau, C. G., SIDS for U.S. Appl. No. 09/674,211, filed Feb. 16, 2001, 1-6.

Mersereau, C. G., Second SIDS for U.S. Appl. No. 09/674,211, filed Sep. 10, 2001, 1-4.

Bockelman, PCT International Preliminary Examination Report for PCT/US99/18861, (Oct. 19, 2000), 1-8.

Kontos, Lina et al., PCT International Search Report for PCT/US02/35354, (May 8, 2003), 1-4.

Ghafoorian, Roz Office Action for U.S. Appl. No. 10/067,623, filed Mar. 20, 2003, 1-5.

Ghafoorian, Roz Office Action for U.S. Appl. No. 10/067,623, filed Jul. 16, 2003, 1-7.

Maiorino, Roz Office Action for U.S. Appl. No. 10/067,623, filed Jan. 18, 2005, 1-4.

Ghafoorian, Roz Office Action for U.S. Appl. No. 10/125,014, filed Jan. 15, 2003, 1-6.

Ghafoorian, Roz Office Action for U.S. Appl. No. 10/125,014, filed Sep. 15, 2003, 1-7.

Maiorino, Roz Office Action for U.S. Appl. No. 10/125,014, filed, Apr. 7, 2004, 1-3.

Ghafoorian, Roz et al., PCT International Search Report for PCT/US09/03282, (Jul. 31, 2003), 1-4.

* cited by examiner

IONTOPHORETIC DRUG DELIVERY SYSTEMS

TECHNICAL FIELD

The present invention relates to methods and apparatus for the controlled delivery of a drug or other beneficial agent in a biological environment. More specifically, the present invention relates to iontophoretic electrotransport devices and methods of their use in delivering fluids to the body tissues of a subject such as by implantation.

BACKGROUND

Numerous systems and techniques have been developed to improve the efficacy and convenience of invasive and non-invasive drug delivery systems. Techniques for delivering drugs include oral administration, direct injection into body tissues, intravenous administration, and transdermal and iontophoretic delivery through the skin. Each type of drug delivery system has its own advantages and disadvantages when compared to the various other delivery systems, and efficacy of the system typically depends on the type of drug and its amenability to the particular delivery technique.

In many cases, drugs such as pharmaceuticals may be administered orally, and the pharmaceutical is designed to be released for absorption by the highly permeable lining of the gastrontestinal system. While advantages of oral ingestion include ease of administration, disadvantages include poor bio-availability due to high "first pass" liver metabolism, the potential for liver toxicity, and the likelihood of drug breakdown and degradation due to digestive processes prior to absorption in the blood stream. Precise control of the release of orally administered drugs is also an issue. Direct injection, using either a hypodermic needle or an injection gun, while allowing for accurate dosing, is not ideal for continuous and convenient drug administration over an extended time period, and may cause recurring pain, trauma and risk of infection to a patient. Commonly used intravenous drug delivery techniques solve the problems of continuous drug administration, but may disadvantageously restrict the patient's mobility. Conventional transdermal systems typically allow for unrestricted patient mobility, but suffer in terms of the types of drugs that can readily diffuse across the relatively impermeable barrier layers of the skin. The stratum corneum layer, in particular, provides the bulk of the resistance to drug permeability. Thus, for drugs in which it is acceptable to administer low dosages over prolonged periods of time, transdermal delivery may prove useful. For the vast majority of drugs, however, this method is not satisfactory due to the low rate at which the drug is absorbed.

In an effort to improve the convenience of drug delivery, provide accurate dosing, and improve drug efficacy, various attempts have been made to improve invasive and non-invasive drug delivery systems. One class of techniques for overcoming the resistive barriers imposed by intact skin is assisted diffusion of a drug through the skin by "electrotransport" processes. Using the principles of electrotransport, a direct electrical current or an electrical potential gradient is used to actively transport the drug transcutaneously into the body.

One method of using electrotransport processes for transdermal drug delivery is known as "iontophoresis." In iontophoresis, the permeation rate (or "flux") of a charged drug compound through the skin surface is controlled by the application of an electrical potential directly across the skin's surface to facilitate the diffusion of a drug across the stratum corneum and into the dermal layers. The efficacy of this process thus depends upon ionizable pharmaceuticals or other drugs (e.g., salts of a pharmaceutical or other drug which, when dissolved, form charged ions).

A second type of iontophoretic electrotransport process called "iontophoretic electroosmosis," involving the transdermal flux of a liquid solvent containing an uncharged drug or pharmaceutical agent, has been recognized as a means for delivery of an uncharged drug or agent into the body. Electroosmosis, in which the solvent convectively moves through a "charged pore" in response to the preferential passage of counter ions, can be induced by the presence of an electric field imposed across the skin by the active electrode of an iontophoretic device.

A third type of electrotransport is known as "electroporation." Electroporation can be used for drug or other agent transport by altering lipid bilayer permeability through the formation of transiently existing pores in the skin membranes.

At any given time during electrically assisted drug delivery, more than one of these electrotransport processes may be occurring simultaneously to some extent. The composition of the stratum corneum, however, is such that its inherent resistance to the flow of electrons is relatively high in comparison to other underlying body tissue (e.g., the further layers of the epidermis and the blood vessels therein). Thus, for certain types of drugs (e.g., some drugs which must remain electrically neutral to retain activity), and especially in the case of large molecule drugs, conventional electrotransport processes through the skin may not result in effective drug delivery. For example, the relatively large size of many protein and peptide molecules make electrotransport exceedingly difficult. Although an increased level of current may assist the protein and peptide molecules across the stratum corneum, such transport may occur at the expense of damaging the molecules (through electric degradation) and/or burning or irritating the skin.

Iontophoresis is typically carried out by establishing an electrical potential using a direct current (DC) between first electrode 18 and second electrode 20. When a voltage is applied from electrodes 18, 20 across the skin tissue surface 30, the current flows from first electrode 18 through the ionized drug solution in reservoir 22, into the skin tissue surface 30, and then back to the second electrode 20, thus creating an electrical circuit by way of body tissues. More specifically, upon activation of iontophoretic system 16, the charged drug is repelled by first electrode 18 through the skin tissue surface 30 (as indicated by the arrows), thereby initiating drug transport by electrostatic repulsion, ionic conduction, and other cooperating electrotransport processes. Thus, positively charged electrodes (anodes) can be used to drive negatively charged drugs, and negatively charged electrodes (cathodes) can be used to drive positively charged drugs.

A typical electrotransport system 16 for the iontophoretic delivery of a drug is shown in FIG. 1. In conventional iontophoresis, a reservoir 22 is provided on a skin tissue surface 30 to serve as a container for a solution of an ionized drug to be electrically transported. A first electrode 18 of a first polarity (e.g., an anode) is placed adjacent the reservoir 22, while a second electrode 20 of a second polarity (e.g., a cathode) is placed in contact with an area of the skin tissue surface 30 which is spaced apart from reservoir 22. A connecting wire 24, and an external power supply (battery) 26 extend between electrodes 18, 20. An ion-conducting adhesive 28 is situated under each electrode 18, 20 for stabilization of the electrodes. Electrolytes are typically added to the solution containing the ionized drug so that current can be easily conducted. A selectively permeable membrane (not shown) may further be placed under electrode 18 to allow for selective flow of particular types of charged and uncharged species into tissue surface 30. A voltage source 24, typically a battery, supplies direct electric current by conductive wires 26 extending to the electrodes.

Iontophoresis is typically carried out by establishing an electrical potential using a direct current (DC) between first electrode 18 and second electrode 20. When a voltage is applied from electrodes 18, 20 across the skin tissue surface 30, the current flows from a first electrode 18 through the ionized drug solution in reservoir 22, into the skin surface 30, and then back to the second electrode 20, thus creating an electrical current by way of body tissues. More specifically, upon activation of iontophoretic system 16, the charged drug is repelled by first electrode 18 through the skin tissue surface 30 (as indicated by the arrows), thereby initiating drug transport by electrostatic repulsion, ionic conduction, and other cooperating electrotransport processes. Thus, positively charged electrodes (anodes) can be used to drive negatively charged drugs, and negatively charged electrodes (cathodes) can be used to drive positively charged drugs.

The electrode driving the ionized drug is commonly called the "donor," or "active," electrode, while the electrode closing the circuit is commonly called the "counter," or "return," electrode. Under alternative configurations, both the anode and the cathode can be used to deliver drugs of the opposite charge. In such a case, both electrodes are considered active or donor electrodes.

Dependent upon molecule size and other factors, neutral drug molecules can also be moved by the application of electrical current, although to a lesser extent than ionized drug molecules, by the forces of electroosmosis and electroporation. During the application of the voltage from electrodes 18, 20, the electrotransport process will steadily continue, with transport abruptly decreasing when the driving force of electrical potential is discontinued.

Exemplary iontophoretic systems are disclosed in U.S. Pat. No. 5,618,265 to Myers et al. and U.S. Pat. Nos. 5,647,844 and 4,927,408 to Haak et al. Other patents discussing a variety of iontophoresis systems, iontophoresis electrodes, and/or methods of iontophoretically administering medicament ions include U.S. Pat. No. 4,250,878 to Jacobsen et al., U.S. Pat. No. 4,474,570 to Ariura et al., U.S. Pat. No. 4,557,723 to Sibalis, U.S. Pat. No. 4,744,787 to Phipps et al., U.S. Pat. No. 4,752,285 to Petelenz et al., U.S. Pat. No. 4,820,263 to Spevak et al., U.S. Pat. No. 4,886,489 to Jacobsen et al., U.S. Pat. No. 4,973,303 to Johnson et al., and U.S. Pat. No. 5,125,894 to Phipps et al., all of which are incorporated herein by this reference.

A continuing need exists to develop drug delivery devices with improved characteristics. Prior art electrotransport transdermal drug delivery devices, while offering convenience in the form of continuous drug dosage and increased mobility for a subject, are still somewhat limited in terms of the efficient delivery of many drugs through the resistive barrier of the stratum corneum. Therefore, a need exists in the art for improved drug delivery systems which are efficacious and site-directed.

SUMMARY OF THE INVENTION

The present invention relates to fluid delivery devices and methods of their use. In a first embodiment, the invention includes an implantable iontophoretic electrotransport device configured for transporting molecules of a drug or other beneficial agent across the tissue of a subject. This device includes a first compartment which is adapted for containing a drug or other beneficial agent and which has an electropositive material configured as a first electrode therein. The first compartment is also adapted to be implanted in whole or in part under a subject's skin surface. The device further includes a second electrode insulated from the first electrode. The second electrode is adapted to be implanted in whole or in part below the subject's skin surface and comprises an electronegative material. At least one insulated conductor provides an electrical interconnection between the first electrode and the second electrode. Disposed under at least a portion of the first compartment is at least one semipermeable membrane configured to be in fluid communication with a drug or other beneficial agent included in the first compartment. The semipermeable membrane is adapted to be implanted under at least a portion of the stratum corneum of a subject.

In one aspect of the embodiment, the semipermeable membrane is substantially microporous, biocompatible, and configured to allow the flow of drug or other beneficial agent molecules therethrough in response to an electric current. The semipermeable membrane is also preferably configured to substantially inhibit transport of molecules of a drug or other beneficial agent in the absence of an electric current delivered to either the drug or other beneficial agent or the semipermeable membrane. The semipermeable membrane may also be configured to allow the flow of ionized or non-ionized molecules of a drug or other beneficial agent therethrough. In another aspect, the semipermeable membrane may comprise a material configured to be resorbable by the body tissues of a subject. A second semipermeable membrane may also be disposed under the second electrode.

The electrodes of the implantable electrotransport device may comprise electrodes configured as a solid, a gel, suspension, or a solution. In one aspect of the embodiment, one of the electrodes is interspersed with a drug or other beneficial agent accommodated in the first compartment of the device. One or both of the electrodes may be formed having a housing comprising a refractory transition metal, such as titanium or tantalum. In this case, the refractory metal electrode housing may be formed as a container for holding the drug or other beneficial agent and/or an electrolyte solution.

A power source may be provided for the electrotransport device. A control circuit, which may include a biofeedback loop and sensor, is also preferably provided.

In an alternate configuration of the electrotransport device, a plurality of electrodes are provided which are adapted to be placed over a skin surface of subject. At least one conductor electrically interconnects the electrodes, and a reservoir adapted to hold a drug or other beneficial agent is disposed under at least one of the electrodes. In this embodiment, a semipermeable membrane disposed adjacently under the reservoir is configured to be implanted under at least a portion of the stratum corneum of a subject.

In various aspects of the alternate embodiment, the semipermeable membrane is configured to substantially inhibit the transport of molecules of a drug or other beneficial agent therethrough in the absence of an electric current. The semipermeable membrane is preferably configured to allow the flow of molecules of a drug or other beneficial agent therethrough in the presence of an electric current. In a related aspect of the embodiment, the semipermeable membrane is configured to allow the passage of ionized or non-ionized molecules of a drug or other beneficial agent. In another aspect of the embodiment, the semipermeable membrane is configured to be substantially microporous, biocompatible, and resistive to blood intrusion. In a still further aspect of the embodiment, the semipermeable membrane comprises a material configured to be resorbable by the body tissues of a subject. A second semipermeable membrane, also configured to be implanted under at least a portion of the stratum corneum of a subject, may be disposed under the second electrode.

A method of electrically facilitating the transport of a drug or other beneficial agent though body tissues of a subject is also provided. The method entails providing a plurality of electrodes configured to conduct electric current in relation to body tissues of a subject; providing at least one drug or other beneficial agent reservoir disposed adjacent an electrically conducting area of at least one of the plurality of electrodes; providing at least one semipermeable membrane in fluid communication with the drug or other beneficial agent reservoir, the semipermeable membrane configured to substantially inhibit passive diffusion of a drug or other beneficial agent therethough in the absence of an electric current applied to either the semipermeable membrane or a drug or other beneficial agent; providing a drug or other beneficial agent in the drug or other beneficial agent reservoir; implanting at least a portion of the semipermeable membrane beneath a stratum corneum skin layer of a subject; responsive to the implanting step, completing a circuit between the plurality of electrodes and transmitting a voltage from the plurality of electrodes and the semipermeable membrane to the body tissues of the subject, whereby the voltage effects transport of the drug or other beneficial agent through the semipermeable membrane and through the body tissues; and delivering the drug or other beneficial agent to the body tissues of the subject.

In various aspects of the method, the semipermeable membrane is configured as a cationic or anionic exchange membrane. The semipermeable membrane may also be configured to have a molecular cutoff adapted to substantially prevent blood intrusion into the semipermeable membrane. The step of implanting the semipermeable membrane may entail implanting substantially the entire cross-section of the membrane beneath a stratum corneum skin layer. Preferably, a portion of the semipermeable membrane remains exterior to the stratum corneum skin layer as a result of the implanting step. In another aspect of the embodiment, implanting the semipermeable membrane comprises implanting a bottom most surface of the semipermeable membrane to a depth approximating about 20-100 μm below the stratum corneum skin layer.

The invention also includes an intraocular delivery device for delivering a beneficial agent to a subject's eye which utilizes liquid present on the subject's conjunctiva as an ionic conductor between two complementary electrodes configured within the device. The intraocular delivery device includes a membrane comprising a semipermeable polymer and having first and second surfaces. The first surface is adapted (e.g., by being flexible, biocompatible, and sized for comfortable fit) to be placed on the subject's conjunctiva to interact with any liquid present thereon. The second surface is configured to contain a beneficial agent for delivery to the subject. A first electrode is in fluid communication with the membrane and beneficial agent, and includes a first electroactive material (e.g., elemental magnesium or zinc). A second electrode comprises a second electroactive material (e.g., carbon). The second electrode is configured to be in fluid communication with the subject's conjunctiva, but, except for conductive material connecting it to the first electrode, is electrically isolated from the first electrode. The first and second electroactive are complementary to each other, and the materials are selected so as to, when configured together as a circuit, to form a battery. When the intraocular drug delivery device is placed on the eye's conjunctiva, any electrically conductive liquid present thereon completes a circuit between said first and second active electrodes, forming the battery, and thus delivering the beneficial agent associated with the flexible membrane to the subject's conjunctiva or cul-de-sac.

Further, the invention includes an intraocular device for delivering a beneficial agent to the back of subject's eye by using the thin skin and mucosa near the eye as semipermeable membrane.

The invention also includes methods of making and using the devices.

BRIEF DESCRIPTION OF THE SEVERAL VIEWS OF THE DRAWINGS

In the drawings, which illustrate what is currently considered to be the best mode for carrying out the invention.

DETAILED DESCRIPTION OF THE PREFERRED EMBODIMENTS

Figure 1:
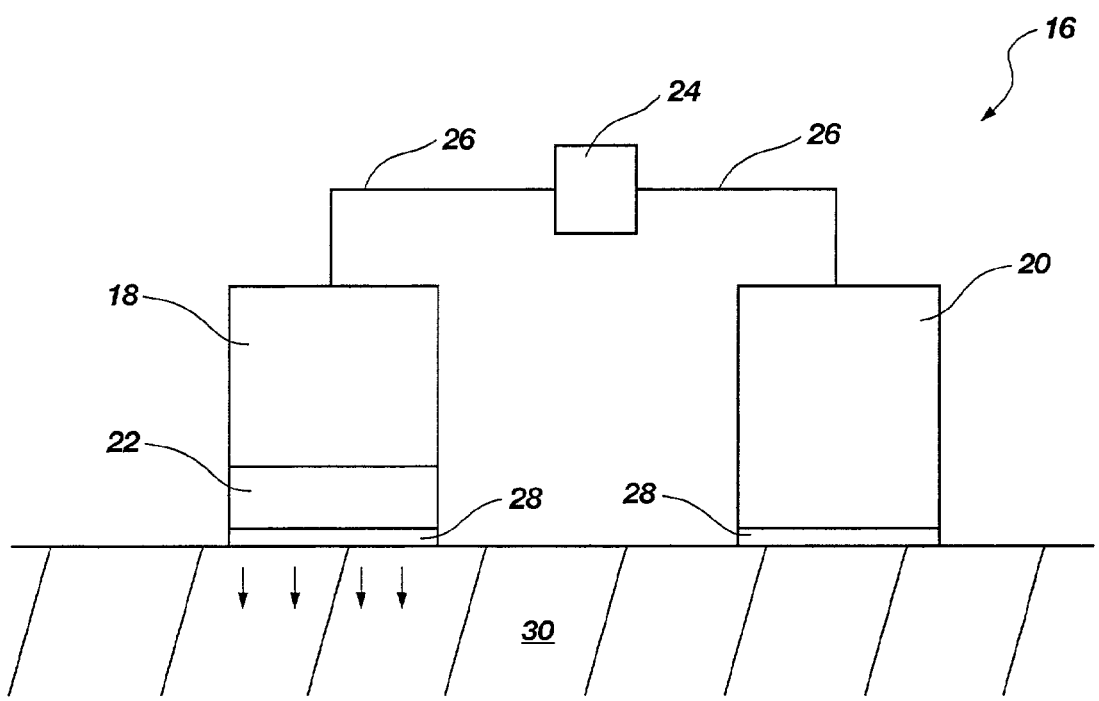
FIG. 1 is a schematic representation of an exemplary prior art transdermal drug delivery device.

The present disclosure relates to improved apparatus and methods of fluid delivery to a subject. In this regard, an electrotransport apparatus, and methods of using the apparatus for drug and other beneficial fluid delivery, are described in relation to the drawing figures. The present disclosure further includes, among other things, novel implantable osmoelectrochemically driven pumps which may be used for site-specific delivery of a drug and other beneficial fluid to a subject.

The term "electrotransport" is used herein to refer to the facilitated migration of ionically charged or uncharged substances across body tissues of a subject upon application of an electric potential to the body tissue. "Electrotransport" thus refers to iontophoresis, electroporation, and electroosmosis transport mechanisms, and combinations of any of these.

Figure 2:
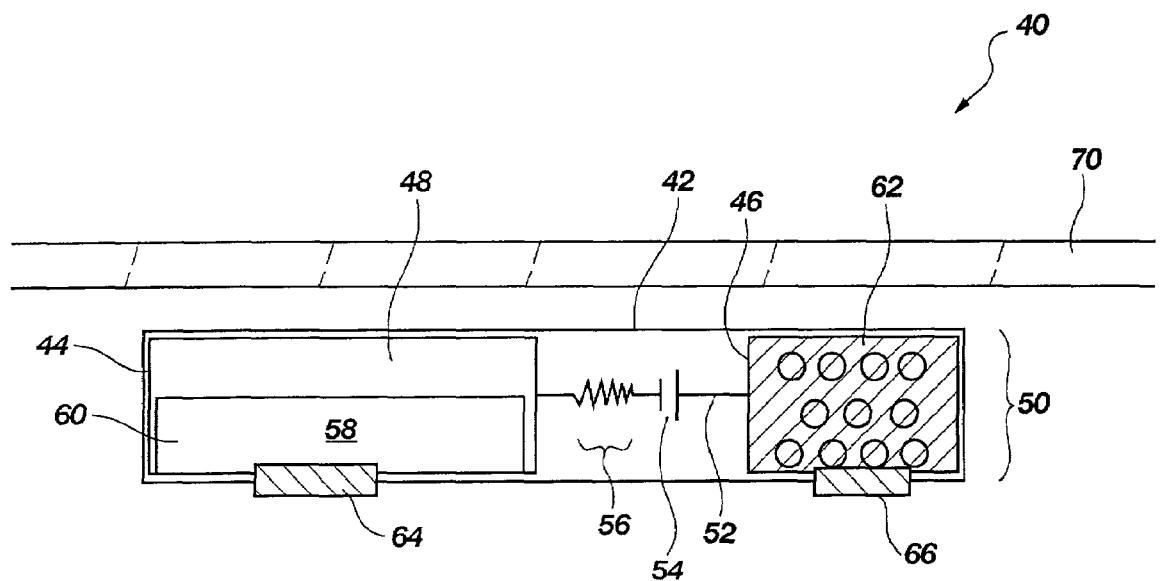
FIG. 2 is a schematic view of a preferred embodiment of an electrotransport device of the present invention.

An embodiment of an electrotransport apparatus 40 of the present invention is illustrated schematically in drawing FIG. 2. Notably, all or part of electrotransport apparatus 40 is configured to be implanted under the stratum corneum 70 of a subject. The electrotransport apparatus includes a supportive unitary housing 42 containing at least two electrically interconnected and spaced apart electrodes 48, 50 of differing electrode potentials (i.e., "active" and "return" electrodes). An insulated conductor 52 (e.g., an insulated copper or aluminum wire) extends between electrodes 48, 50 to provide an electrical interconnection. In the illustrated embodiment, electrodes 48, 50 are connected through insulated conductor 52 to a power source 54 (e.g., a battery, series of batteries or other power source) configured to provide sufficient electrical current to facilitate the electrotransport of a drug or other beneficial agent across tissues of a subject. A control circuit 56, comprising at least a current limiting resistor, is preferably interposed in insulated conductor 52 between electrodes 48, 50.

Still referring to FIG. 2, a first electrode 48 includes an electropositive material contained in, or interspersed in, a first compartment 44 of electrotransport apparatus 40. A second electrode 50 includes an electronegative material contained in, or interspersed in, a second compartment 46 of electrotransport apparatus 40. First and second compartments 44, 46 are encompassed within a unitary housing 42. Also contained in at least one of first compartment 44 and second compartment 46 is a drug or other beneficial agent 58, preferably provided in fluid form (shown in FIG. 2 as residing within first compartment 44). First compartment 44 and second compartment 46 comprise reservoirs 60, 62 configured to hold drugs or other beneficial agents 58 and/or electrolyte solutions for conducting current from electrodes 48, 50. Solutions, solids, suspensions, or gels of electropositive and electronegative materials comprising electrodes 48 and 50, respectively, may reside in reservoirs 60, 62, and/or in separate portions of first and second compartments 44, 46. Thus, the present invention contemplates that a drug or other beneficial agent 58 may occupy its own separate compartment, or share a compartment 44, 46 with an electrode and/or an electrolye.

Semipermeable membranes 64, 66 are disposed adjacently under each of first and second compartments 44, 46. In the illustrated embodiment, semipermeable membrane 64 is provided in fluid communication with the drug or other beneficial agent 58 contained in reservoir 60 of first compartment 44.

According to the invention, electrotransport apparatus 40 is implanted, in whole or in part, at least under the uppermost portion of the stratum corneum 70 of a subject. The underlying body tissues of the subject complete an electrical circuit between electrodes 48, 50. Power source 54 and electrodes 48, 50 may then deliver direct current to the body tissues of the subject either continuously, or during intermittent time intervals. Application of the electric current from electrodes 48, 50 facilitates the migration of the drug or other beneficial agent 58 through semipermeable membrane 64 and into the underlying and/or surrounding tissues of the subject, with the extent of the migration being proportional to the duration of the current application and the current density. The voltage transferred by electrodes 48, 50 increases the rate of intradermal and/or subdermal flux by reducing the physical resistance and enhancing the permeability of underlying and/or surrounding tissue layers. Thus, the current path facilitates the movement of drug or other beneficial agent 58 through desired tissues in a site-specific manner. Depending upon the implanted location of electrotransport apparatus 40, the voltage path directed by electrodes 48, 50 may aid in transporting drug or other beneficial agent 58 through body tissues and into the systemic circulation of the subject.

As used herein, an "electronegative material" is a material having a relative tendency to attract electrons to itself, while an "electropositive material" has a relative tendency to release electrons. In FIG. 2, electrode 48 is shown as an electropositive "anode" electrode, while electrode 50 is shown as an electronegative "cathode" electrode. Connection of electrodes 48, 50 to power source 56, and completion of a circuit between the electrodes 48, 50, thus causes "anode" electrode 48 to release electrons which travel transdermally under stratum corneum 70 to seek the positively charged (electronegative) "cathode" electrode 50.

Electrode materials contemplated for use herein include electropositive and electronegative materials provided in electrolyte solutions, suspensions, and gels, as well as electrode materials provided as solids. Preferred electropositive (anode) materials for use in the present invention include the class of alkali metals, as well as various electropositive metals located on the right side of the periodic chart, such as Zn, Mg, and Al. In a preferred embodiment, the anode electrode comprises an electronegative metal such as Zn, Mg, Ca, Ba, Al, Sn, Fe, or combinations or alloys thereof, as a mixture in a solution, suspension, or in a gel, which may be combined with a solvated drug or other beneficial agent 58 contained in reservoir 60. Electronegative materials for use in the present invention include carbon, halides, chalcogenides and active metal oxides such as silver oxides, copper oxides, manganese dioxides, and mixtures and composites of any thereof.

The term "electrolyte," as used herein, refers to any material that provides ionic conductivity, and through which an electric current can travel, and/or through which an electrochemically active species can diffuse. The electrolyte can be, for example, a solid, liquid, or semi-solid (e.g., in the form of a gel) material, which can be composed primarily of water and ions (e.g., sodium chloride), and generally comprises 50% or more water by weight. The electrolyte can be in the form of a gel, a sponge or pad (e.g., soaked with a conventional electrolytic solution), or any other material that can contain an electrolyte and allow passage therethrough of electrochemically active species.

As previously discussed, contained in at least one of reservoirs 60, 62 is a drug or other beneficial agent 58 which is preferably provided in fluid or gel form. The drug or other beneficial agent 58 shown in reservoir 60 may be ionized or non-ionized. Reservoirs 60, 62 may embody any conventional reservoir type known in the art, including, but not limited to, reservoirs comprising a pouch cavity, porous sponge or pad, gel matrix, or hydrophilic polymer. The reservoir may also include so-called "permeation enhancers" to increase the permeability of the skin for delivery of the drug.

Figure 3:
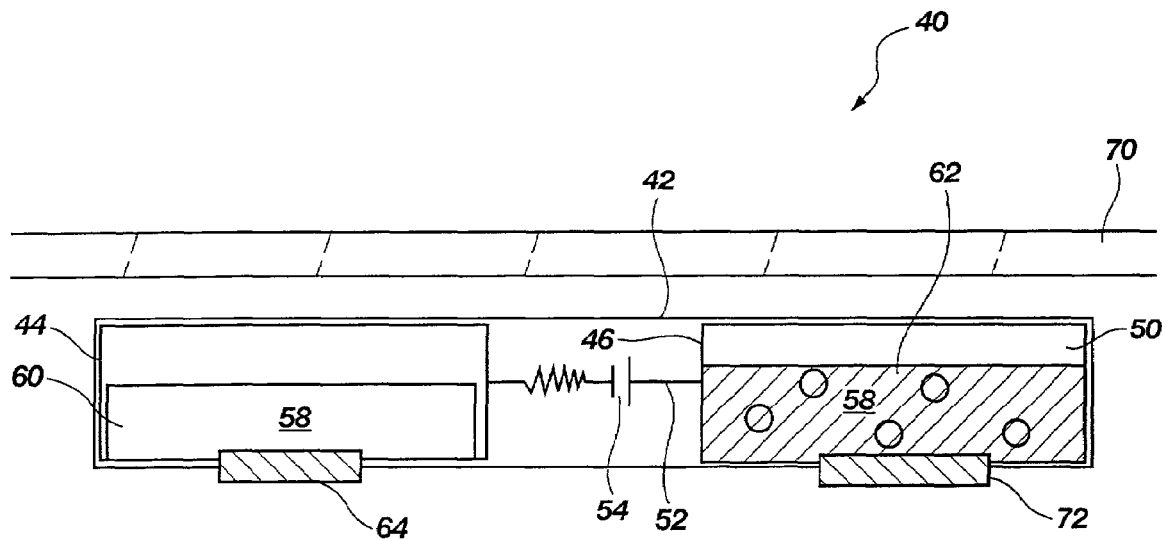
FIG. 3 is a schematic view of an alternate embodiment of the electrotransport device of the present invention.

As illustrated in an alternate embodiment shown in FIG. 3, the second reservoir 62 may also contain a drug or other beneficial agent 58, such that a drug or beneficial agent 58 is located under, adjacent, or intermixed with, each of electrodes 42, 44. In this embodiment, a semipermeable membrane 72 is provided in fluid communication with reservoir 62 for the delivery of the drug or other beneficial agent therethrough. Thus, drug or other beneficial agent delivery occurs from both electrodes 48, 50 upon completion of an electrical circuit therebetween. Charged (ionized) or uncharged drugs or other beneficial agents may be provided in reservoir 62. The electrotransport apparatus configuration described below for iontophoretic delivery of a drug or other beneficial agent is equally applicable to the embodiment shown in FIG. 3.

In an iontophoretic electrotransport configuration of electrotransport apparatus 40 (see, FIG. 2), the drug or other beneficial agent 58 is provided in an ionic ("charged") form. In this situation, either the anode electrode 48 or the cathode electrode 50 may function as the "donor" electrode from which the drug is delivered (electrostatically repelled) via iontophoresis. The other electrode, which possesses an opposite charge, may then function as a "return" electrode which closes the circuit. For example, negatively charged drugs will be repelled into a subject's tissues by a negatively charged anode "donor" electrode, while positively charged drugs will be repelled by a positively charged cathode "donor" electrode. In an iontophoretic configuration, the drug or other beneficial agent 58 will generally be provided in, or overlying and adjacent to, an electrolyte solution conducive to the passage of ions of the drug or other beneficial agent 58. The drug or other beneficial agent 58 may also or alternatively be provided in a hydrophilic, electrolyte-containing gel or gel matrix or absorbent material. When electrically connected to the donor electrode, the contents of the drug or other beneficial agent reservoir thus provide a source of one or more ionic species for electrotransport. Because protons and hydroxyl ions may evolve at the anode and cathode electrodes, respectively, suitable buffers may be provided in the drug or other beneficial agent solution, suspension or gel.

The drug or other beneficial agent 58 may also be provided in liposomal formulations, the potential advantages of which include enhanced electrotransport across tissues and solubilization of poorly water-soluble drugs. Further advantageously, non-ionized drugs may be encapsulated in charged liposomes, allowing efficient delivery by electrostatic repulsion (iontophoresis). For drugs or hormones not susceptible to ionization, appropriate carriers may also be used to provide an ionic charge (e.g., pyridine compounds capable of forming a quaternary amine salt upon oxidation of a nitrogen on a heterocyclic ring). As used herein, the term "drug or other beneficial agent" is given its broadest meaning, and includes all types of agents, medicines, pharmaceuticals, biologics, and other substances having a beneficial, therapeutic, or desired physiological effect on a subject.

Semipermeable membranes 64, 66 are preferably configured to conduct current flowing between electrodes 48, 50 under stratum corneum 70 in furtherance of the completion of an electrical circuit under stratum corneum 70. Thus, semipermeable membranes 64, 66 are preferably configured to have a sufficiently low voltage drop across the membranes so as to enable power source 54 to deliver current to underlying body tissues. To increase their conductivity, semipermeable membranes 64, 66 may be embedded with an appropriate electrolyte and/or otherwise formed of suitable current-conducting materials known in the art (e.g., modified cellulose acetate resins).

Referring again to FIG. 2, semipermeable membrane 64 is disposed under reservoir 60 such that a first surface of semipermeable membrane is in fluid communication with the contents of reservoir 60 and in current conducting relation to electrode 48. A second surface of the semipermeable membrane 64 extends outwardly away from reservoir 60. Semipermeable membrane 66 is disposed adjacent reservoir 62 and in current conducting relation with electrode 50.

As all or part of electrotransport apparatus 40 is adapted to be placed under the stratum corneum 70 of a subject, housing 42 and semipermeable membranes 64, 66 are formed of biocompatible materials. Furthermore, housing 42 and semipermeable membranes 64, 66 may be pre-treated with germicides and fungicides in a manner known in the art, and/or formed of, or layered with, known materials which are resistant to microorganisms. An electrotransport apparatus 40 containing semipermeable membranes 64, 66 thus advantageously allows molecules of drugs or other beneficial agents 58 to bypass the resistive stratum corneum layer of the skin, while simultaneously protecting against unwanted infection and immune reactions.

Referring to FIGS. 2 and 3, semipermeable membranes 64, 72 are configured to prevent the passive release of drug or other beneficial agent 58 from reservoirs 60, 62 when the electrotransport apparatus 40 is not in operation. Preferably, semipermeable membranes 64, 72 are further adapted to limit and/or regulate the rate of the drug or other beneficial agent 58 therethrough. Thus, semipermeable membranes 64, 72 provide a means to control the rate of drug diffusion through and into the tissues of a subject. In a preferred embodiment, the drug diffusion control provided by semipermeable membranes 64, 72 may be used for reducing and/or increasing dosages for drugs of varying potencies, dependent upon a particular subject's needs. For example, certain drugs which are highly potent may require very low dosing requirements. Similarly, tissue which has been compromised in some fashion may have higher or lower dosing requirements than tissue which is intact. Additionally, a subject who has not satisfactorily responded to a particular drug dosage may require increased dosages of a drug transmitted through semipermeable membrane.

At a minimum, semipermeable membranes 64, 72 prevent passive diffusion of the drug or other beneficial agent in the absence of a moving force (e.g., iontophoresis). Semipermeable membranes 64, 72 are preferably adapted to be substantially microporous throughout, advantageously providing relatively uniform drug or other beneficial agent 58 delivery to underlying and surrounding body tissue of a subject. In a preferred embodiment for iontophoretic drug delivery, semipermeable membranes 64, 72 are formed of microporous materials having a pore size of less than about 1 µm, including dialysis membranes, polycarbonate, polysulfone, cellulose acetate, polyacrylonitrile, polyurethane, elastomers, polyolefin, fluoropolymers, and the like, with dialysis membrane and polysulfone as the preferred materials for iontophoresis.

Semipermeable membranes 64, 72 are further configured prevent blood and other body fluids and components from diffusing through the membranes and into reservoirs 60, 62 containing electrolytes and/or drugs or other beneficial agents 58. In this aspect of the embodiment, the large number of micropores on semipermeable membranes 64, 72 reduce the likelihood that a significant surface area of semipermeable membranes 64, 67 will become blocked with blood components, proteins, and other molecules, fragments, or material from within a subject's body. Also in this regard, semipermeable membranes 64, 72 are preferably configured to have molecular cutoffs ranging from about 100 to about 50,000 daltons. Most preferably, semipermeable membranes 64, 72 will have molecular cutoffs ranging from about 200 to about 40,000 daltons. As a further precaution, semipermeable membranes 64, 72 may be treated with anti-clotting factors, and other materials which limit or prevent occlusion, protein adhesion, etc., as are known in the art.

In another aspect of the embodiments shown in FIGS. 2 and 3, semipermeable membranes 64, 72 are configured to be substantially impermeable to the ionic form of the drug or other beneficial agent. When an electrical current is applied to the active and return electrodes 48, 50, the drug or other beneficial agent 58 changes from its ionic form to a non-ionic form and then passes through the membrane.

In a further aspect of the subject embodiments, a current applied to semipermeable membranes 64, 72 renders the membranes permeable to the ionized form of the drug or other beneficial agent 58. Thus, in the situation where a charged drug is to be delivered, semipermeable membranes 64, 72 may be configured as a cationic or an anionic exchange membrane. For example, a drug or other beneficial agent 58 which is positively charged will be retained by a cation exchange membrane in the absence of a current. When a current is applied to the cation exchange membrane through electrodes 48, 50, the membrane loses or reverses its charge to allow the charged drug or other beneficial agent 58 to pass therethrough. Preferred ion exchange membranes for use in the present invention comprise resins containing ion exchange functional groups such as: quarternary amines (e.g., AG 1-X8 available through Bio-Rad, Richmond, Calif.), imidodiacetic acid (e.g., Serdolit® available through Crescent Chemical, Hauppague, N.Y.), carboxylic acid (e.g., Bio-Rex® available through Bio-Rad, Richmond, Calif.), and sulfonic acid (e.g., Spectra/Por Ion Selective Membrane® available through Spectrum Laboratories, Rancho Dominguez, Calif.).

The semipermeable membrane may also be formed, in part, as a material which is resorbable by body tissues of subject. Resorbable materials may be applied, for example, to outer surfaces of semipermeable membranes 64, 72 such that the materials prevent the release of a drug other beneficial agent 58 prior to implantation in a subject's body tissues. Upon hydrolytic breakdown in the subject's body of the polymer matrix of the resorbable materials, the drug or other beneficial agent is ready for electrotransport. For example, semipermeable membranes 64, 72 may be coated with, or otherwise formed in part by, a material constituted by polylactic, polyglycol or polygalactoside acid, or other various resorbable polymers known in the art, which preferably lack degradation products causing inflammation or toxicity when placed under the stratum corneum (see, for example, U.S. Pat. No. 3,773,919, the disclosure of which is incorporated in its entirely herein).

To provide additional strength to semipermeable membranes 64, 66, 72 (FIGS. 2 and 3), if necessary, the semipermeable membranes can be supported, for example, by a suitable screen or mesh which does not affect the drug or other beneficial agent release characteristics (e.g., by a having a substantially larger pore size), including any ion exchange characteristics, of semipermeable membranes 64, 72.

The semipermeable membranes 64, 66, 72 used in the present invention can be manufactured as an integral part of the housing 42 or the drug reservoir 60, 62 of electrotransport apparatus 40, or may be manufactured separately and firmly attached to the housing 42 or drug reservoir 60, 62 by means known to those of skill in the art (e.g. by suitable adhesives).

Referring again to both FIGS. 2 and 3, housing 42 can be a supportive, molded plastic case or other suitable structure which is insulative of electrodes 48, 50, and which does not interfere with the transmission of electric current to underlying tissues of a subject. Thus, housing 42 does not cover at least a portion of a bottom most area of electrotransport apparatus 40, including semipermeable membranes 64, 66, 72. Housing 42 is further preferably configured of a size and shape known in the art (e.g., provided in thin small outline form) which allows electrotransport apparatus 40 to remain in an implanted state for an indefinite period of time without interfering with the normal daily activities of the subject, and with little or no discomfort and physiological reaction to the implanted device.

Housing 42 is preferably made from inert, non-erodible and bio-compatible materials such as thermoplastic polymers (e.g., polypropylene, polyethylene, polytretrafluorotethene (PFTE), polyfluoroethylene, polyvinyl chloride, etc.), ethylene vinylacetate, polyvinylpirrolidone, polyacrylamide, cellulosic derivatives (e.g., cellulose esters, cellulose ethers, cellulose acrylate, cellulose acetate, cellulose butyrate, cellulose propionate, ethylcellulose, hydroxypropyl methylcellulose), and mixtures of thereof. Non-toxic polymeric resin coatings, such as silicone rubber, ceramic materials or blends thereof (e.g., hydroxyapatite blends) may also be using in fabrication of housing 42. Preferably, housing 42 is formed as a rigid or semi-rigid container encompassing both first compartment 44 and second compartment 46. It is also contemplated that a separate housing 42 may be provided over each of compartments 44, 46, or that housing 42 may be provided in a substantially flexible form, for example, so as to adapt to the contours of a subject's body.

Housing 42 may be manufactured by a variety of processes well known in the art, including vacuum forming, injection or compression molding, and other standard techniques for manipulation of thermoplastic polymers.

Figure 4:
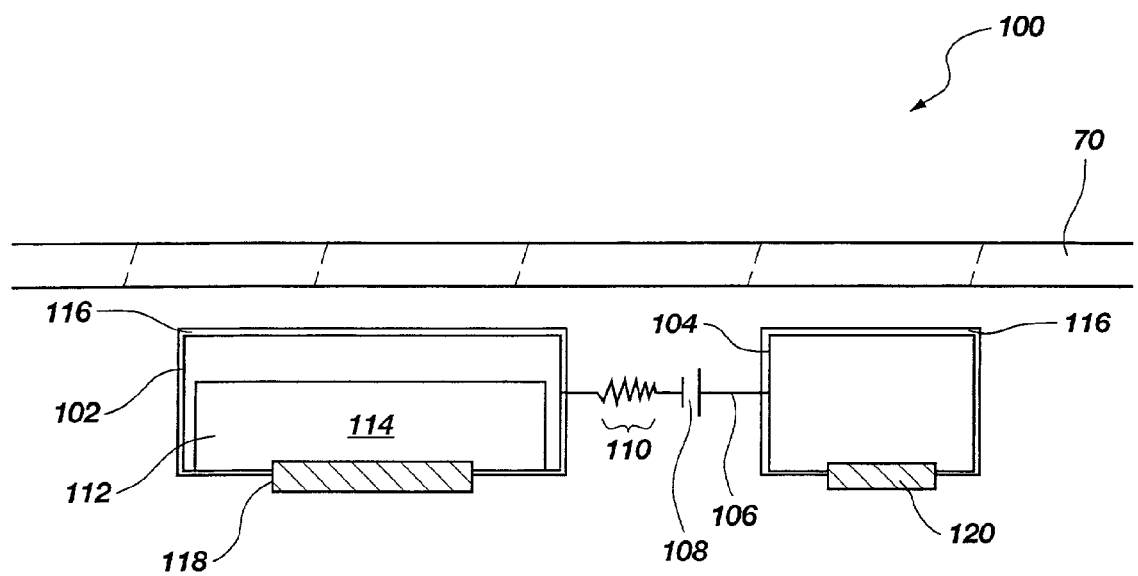
FIG. 4 is a schematic view of an alternate electrode embodiment of the electrotransport device of the present invention.

In a still further embodiment illustrated in FIG. 4, an implantable electrotransport device 100 comprises at least one first electrode 102 which is formed with an exterior comprising a refractory transition metal, such as titanium, tantalum, etc. Contained inside the exterior is an electrode material such as zinc, aluminum, or maganese. A second electrode 104, which is insulated from electrode 102, is electrically interconnected with electrode 102 by an insulated conductor 106. A power source 108 (e.g., a battery or a series of batteries), and an optional control circuit 110, are interposed between electrodes 102, 104 by way of insulated conductor 106.

In this embodiment, first electrode 102 is formed as having a metal housing which contains a cavity 112 therein configured for holding and/or storing a drug or other beneficial agent 114. The exterior of second electrode 104 is preferably formed of the same metal(s) (e.g., titanium, tantalum) as electrode 102. Electrode materials within the exterior of the second electrode 104 may include active metal oxides, halides, and chalcogenides. Typically, first electrode 102 will be relatively larger than second electrode 104 due to the volume of the cavity 112 for containing the drug or other beneficial agent 114. Each of electrodes 102, 104 are provided with a biopolymer coating 116 known in the art to be suitable for implantation under the stratum corneum 70 of a subject. A unitary or separate polymer housing (not shown) may optionally be provided over side and top portions of electrodes 102, 104, leaving at least a portion of a bottom most area of each of electrodes 102, 104 exposed, such that an electric current may be delivered to underlying and/or surrounding body tissues therefrom. In this regard, electrodes 102, 104 may further comprise electrolytes to facilite the conduction of an electric current upon an application of voltage from electrodes 102, 104. Semipermeable membranes 118, 120 are disposed under each of first electrode 102 and second electrode 104, with semipermeable membrane 118 provided in fluid communication with a drug or other beneficial agent 114 contained in cavity 112. Semipermeable membranes 118, 120 are preferably configured as previously described in relation to FIG. 2.

Typically, the entirety of electrotransport apparatus 100 is implanted at least under the uppermost portion of the stratum corneum of a subject, whereby an electrical circuit is completed between the electrodes 102, 104. Electrotransport apparatus 100 thus begins to operate by way of voltage conducted from power source 108 through insulated conductor 106. An electric potential (either direct current or a more complex waveform) is thus applied between electrodes 102, 104. The electrode material in electrode 102, upon receiving the electron flow from power source 108, is capable of acting as an electropositive electrode which releases electrons into underlying and/or surrounding areas of body tissues. Conversely, electrode material in electrode 104, acts as an electronegative electrode when the electrical circuit is completed, and consequently receives the electrons transmitted through the body tissues from first electrode 102.

As previously described, the movement of drug or other beneficial agent 114 through semipermeable membrane 118 and into the body tissues is facilitated by the electric current generated by first and second electrodes 102, 104 and power source 108. Also as previously described, uncharged drugs may be used in the subject device. Alternatively, charged drugs or other beneficial agents 114 may be used for iontophoretic delivery through the tissues, and semipermeable membrane 118 may be adapted accordingly (e.g., as an ion exchange membrane) for such use. Of course, second electrode 104 may be adapted with a drug-containing cavity in a manner similar to that of first electrode 102, thus allowing for drug delivery from both of electrodes 102, 104.

Figure 5:
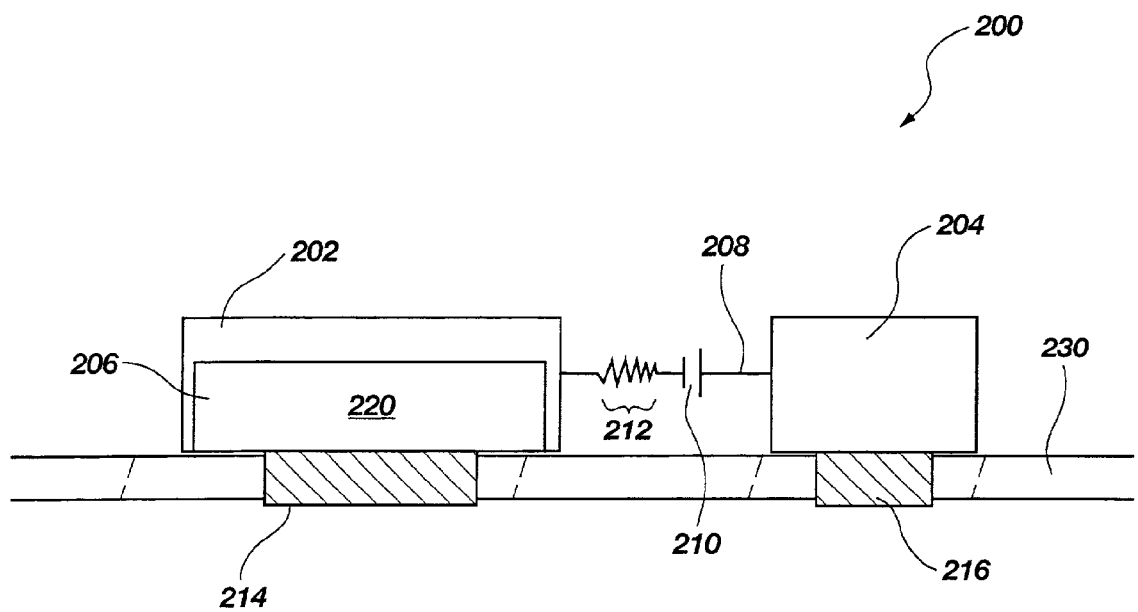
FIG. 5 is a schematic view of a second preferred embodiment of an electrotransport device of the present invention.

In an embodiment of an electrotransport apparatus 200 shown in FIG. 5, spaced apart electrodes 202 and 204, a drug or other beneficial agent reservoir 206, and semipermeable membranes 214, 216 are configured in a manner as described in, or substantially similar to, the embodiments found in any of FIGS. 1-4. Thus, semipermeable membranes 214, 216 are preferably configured to prevent the passive release of a drug or other beneficial agent 220 from reservoirs 206 when electrotransport apparatus 200 is not in operation, and to conduct current from electrodes 202, 204 when the device is activated. Semipermeable membranes 214, 216 are preferably further adapted in the manner previously described to limit and/or regulate the rate of the drug or other beneficial agent therethrough during activation of the device, and thus provide a means to control the rate of drug diffusion into the underlying tissue of a subject. An insulated conductor 208, power source 210 and optional control circuit 212 extend between electrodes 202, 204 in the manner previously described to effect a source of voltage and electrical interconnection to electrodes 202, 204. An electrolyte (not shown) is preferably disposed adjacent electrode materials in electrodes 202, 204 to facilitate electrical conduction therefrom.

In this embodiment, however, electrodes 202, 204 are configured to be placed over a skin surface (stratum corneum layer) 230, while at least a part, and preferably substantially all, of semipermeable membranes 214, 216 are configured to be implanted under at least a part of the stratum corneum layer 230 of the skin of a subject.

As illustrated in FIG. 5, a first surface 222 of semipermeable membrane 214 is disposed under a drug or other beneficial agent reservoir 206, and in fluid communication with a drug or other beneficial agent 220 contained therein. A second surface 224 of semipermeable membrane 214 is configured to extend downwardly past the stratum corneum layer 230. Preferably, the cross-section of semipermeable membrane 214 (i.e., the distance extending between first surface 222 and second surface 224) is at least greater than about 15 µm. A cross-section of at least this approximation will typically extend beyond the upper portion of the stratum corneum of most human subjects. This embodiment is particularly advantageous in that the uppermost 15 µm of the stratum corneum provides substantially the greatest amount of resistance to drug diffusion and the flow of an electrical current. Of course, greater or lesser cross-sections can be used for semipermeable membrane 214, dependent upon the skin type and skin characteristics of the subject, as well as the type of drug or other beneficial agent to be delivered. For example, higher molecular weight drugs or other beneficial agents (e.g., over 40,000 daltons) may require semipermeable membrane 214 to be implanted to a depth greater than 15 µm, and thus require semipermeable membrane 214 to have a cross-section somewhat or substantially greater than 15 µm. Preferably, semipermeable membrane 214 is implanted such that second surface 224 extends downwardly to a depth approximating about 20-100 µm below the stratum corneum skin layer.

Semipermeable membrane 216 is disposed adjacent electrode 204, and in current conducting relation therewith. Semipermeable membrane 216 is also configured to be implanted at least to a depth of about 15 µm into the stratum corneum. Thus, the cross-section of semipermeable membrane 216 is also configured to be at least about 15 µm.

As previously described in relation to FIGS. 2-4, semipermeable membranes 214, 216 are preferably formed of biocompatible materials with very low toxicity. In preferred aspect of the embodiment, semipermeable membranes 214, 216 are configured to act as "artificial skin" layers when implanted in the stratum corneum. Thus, semipermeable membranes 214, 216 are typically implanted to a depth such that at least an upper most surface portion of semipermeable membranes 214, 216 is substantially level with the exterior of the skin (see, FIG. 5). As an "artificial skin," semipermeable membranes 214, 216 will preferably be impervious to water and a wide range of microorganisms, thus serving to provide a barrier function for tissue underlying semipermeable membranes 214, 216.

In use, electrodes 202, 204 of electrotransport apparatus 200 are placed on a stratum corneum surface 230 of a subject, with semipermeable membranes 214, 216 implanted below at least an uppermost layer of stratum corneum 230. Areas of an assembly containing electrodes 202, 204 may be attached to the stratum corneum surface 230, for example, using pressure sensitive adhesives (not shown) known in the art. Placement of semipermeable membranes 214, 216 below the stratum corneum 230 surface completes an electrical circuit between electrodes 202, 204. A voltage supplied by power source 210 creates an electric potential (either direct current or a more complex waveform) between electrodes 202, 204. Current thus flows from the first electrode 202, through the drug or other beneficial agent reservoir 206, through semipermeable membrane 214, and into the underlying and/or surrounding tissue of the subject. The current follows a path which flows back through semipermeable membrane 216 to the "return" electrode 204. The current flow electrically assists the transport of drug or other beneficial agent 220 to underlying and/or surrounding tissues of the subject in the manner previously described (e.g., by iontophoresis, electroporation, and electroosmosis transport mechanisms, and combinations of any of these).

Because semipermeable membranes are 214, 216 are located below at least an upper layer of the stratum corneum, relatively high molecular weight drugs and other therapeutic agents can be delivered to tissues of a subject using the electrotransport apparatus of the present invention. For example, the present invention may be used for the controlled delivery of various macromolecular substances, such as peptides and proteins, having molecular weights of greater than 40,000 daltons.

Figure 6:
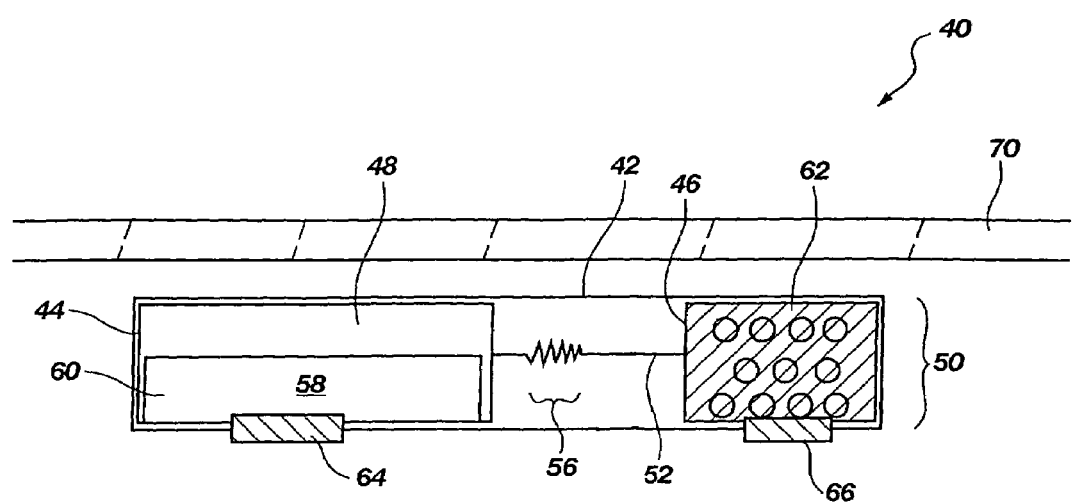
FIG. 6 is a schematic view of another embodiment of an electrotransport device of the present invention.

Once being apprised of the instant embodiments of the invention, various methods of making and using the invention will become apparent to one of ordinary skill in the art. For example, the described devices can be easily modified such that the electric potential between the first and second electrodes is created by forming the electrodes of electrochemically active materials, thus establishing an electrochemical (galvanic) cell. In this embodiment (FIG. 6), an external power supply is unnecessary, but may be optionally provided to boost the voltage delivery of the device. The described electrotransport apparatus may also be easily adapted to be placed in body cavities, ingested, placed on the buccal tissue, surgically implanted adjacent deep tissue in the body of a subject, and the like. Furthermore, the control circuit of the apparatus may be configured with a sensor for biofeedback control, such that drugs or other beneficial agents are released in response to a physiological demand.

The electrotransport apparatus of the present invention contemplates that a plurality of semipermeable membranes may be disposed under each of the active and return electrodes for some applications, with some or all of the semipermeable membranes configured to be implanted below the stratum corneum surface.

In one particularly preferred embodiment, the intraocular delivery version of the invention, the device for delivering a beneficial agent is, for example, placed on a subject's eye (e.g., on the conjunctiva particularly in the cul-de-sac of the eye) and uses liquid present on the subject's conjunctiva (e.g., lacrimal fluid, tears, or an exogenously applied ionic solution such as artificial tears) to complete the circuit between the two complementary electrodes. Preferably, the device is placed so as not to interfere with the subject's eye sight.

The intraocular drug delivery device is sized to fit relatively comfortably on a subject's conjunctiva. It is preferably sized so that the subject can easily and comfortably open and close his or her eyelid without discomfort or interference with vision, and is sized accordingly. The device is preferably sized and shaped to fit within the cul-de-sac of the subject's eye (e.g., it can have an eliptic shape), and will accordingly differ in size with different species of subject.

The device includes a semipermeable flexible membrane, with first and second surfaces and a periphery. The membrane is preferably made of a pyrogen-free polymer capable of releasing drug or other beneficial agent therethrough (e.g., polyethylene, polypropylene, hydrophobic ethylene/vinyl acetate co-polymer membrane (with or without di(2-ethylhexyl-2-phthalate), or other polymeric material used to make, for example, contact lenses), which membrane is associated with the beneficial agent for delivery to the subject's eye. The beneficial agent can be "associated with" the membrane, by, for instance, being included in a reservoir with the first electroactive material (e.g., Zn or Mg) or being imbedded, admixed or dissolved in the membrane.

A second active electrode (e.g., carbon) is also associated near the periphery of the intraocular drug delivery, located at a position distal to the first active electrode, but still in fluid communication with the surface of the membrane to be placed in contact with the conjunctiva.

A conductor (or semi-conductor), insulated from the flexible membrane's first surface, extends between the first and second active electrodes, and provides an electrical interconnection therebetween. The conductor can be a metal such as copper, aluminum, or iron.

The conductor may be associated with a resistor (or other circuitry) to control the release of drug or beneficial agent from the drug delivery device as previously described herein.

When the intraocular drug delivery device is placed on the eye's conjunctiva or cul-de-sac, any electrically conductive liquid present completes a circuit between said first and second active electrodes, forming the battery, and thus delivering the beneficial agent associated with the flexible membrane to the subject's conjunctiva or cul-de-sac.

Drugs and other beneficial agents for administration into a subject's eye include pilocarpine nitrate, carbachol, acelidine HCl, acetylcholine chloride, pilocarpine HCl, echothiophate iodide, isoflurophate, physostigmine, physostigmine salicylate, physostigmine sulfate, antibiotics, antihypertensives, peptides for systemic administration such as insulin, etc. Of course, the amount of drug or other beneficial agent contained within the device for ocular administration will depend on the species, condition and age of the subject to be treated, the drug or other beneficial agent chosen, the condition to be treated with the drug or beneficial agent, etc. For example, in the case of pilocarpine nitrate (to decrease intraocular pressure in an adult human's eye), the entire device can contain 5 mg of pilocarpine, and release 20 µg per hour for a week. Alternatively, it can contain 11 mg of pilocarpine and release 40 µg per hour for a week if need be.

The device can be advantageously used with an exogenous or supplemental ionic fluid, such as artificial tears, isotonic solutions, saline solutions, etc.

It will be appreciated by those skilled in the art that the embodiments herein described, while illustrating certain embodiments, are not intended to so limit the invention disclosed herein or the scope of the claims. Those skilled in the art will also recognize that various combinations or modification of the preferred embodiments could be made without departing from the scope of the invention.

What is claimed is:

1. An implantable electrotransport comprising:
a first electrode comprising an electropositive material in operable communication with an ionic fluid;
a second electrode comprising an electronegative material in operable communication with said ionic fluid;
a bio-compatibile semipermeable membrane disposed adjacently under at least a portion of either said first electrode or said second electrode, said semipermeable membrane configured to be in fluid communication with said ionic fluid in an environment in which said electrotransport device is placed;
a compartment adapted for containing a beneficial agent therein, the compartment in operable communication with said first or second electrode, said semipermeable membrane configured to be in fluid communication with any beneficial agent contained in said compartment; and
a conductor, insulated from said ionic fluid, said conductor extending from said first electrode to said second electrode and providing an electrical interconnection therebetween;
wherein said electropositive material, said electronegative conductor and said ionic fluid complete a circuit capable of creating a current beneath a stratum corneum skin layer sufficient to transport said beneficial agent through said membrane without an additional power source.

2. The electrotransport device of claim 1, wherein said compartment has portions formed of a refractory transition metal configured as an electrode housing, said portions coated with a biocompatible material.

3. The electrotransport device of claim 2, wherein said electrode housing is formed of the same refractory transition metal as the first electrode.

4. The electrotransport device of claim 2, wherein said portions are formed of a metal selected from the group consisting of titanium and tantalum.

5. The electrotransport device of claim 1, further comprising a power source in electrical communication with said first electrode.

6. The electrotransport device of claim 5, further comprising a control circuit interposed in said electrical connection between said power source and said first electrode.

7. The electrotransport device of claim 1, wherein said semipermeable membrane is configured to allow flow of molecules from said compartment to the ionic fluid responsive to an electric current delivered thereupon.

8. The electrotransport device of claim 1, wherein said semipermeable membrane is configured to substantially inhibit transport of the molecules therethrough in the absence of an electric current delivered to one of the molecules and said semipermeable membrane.

9. The electrotransport device of claim 1, further comprising a second semipermeable membrane disposed adjacently under said second electrode.

10. The electrotransport device of claim 1, wherein said semipermeable membrane is configured to conduct charged species from said first electrode when implanted under a subject's skin surface in whom the electrotransport device has been implanted.

11. The electrotransport device of claim 1, wherein said at least one semipermeable membrane is configured to be substantially microporous throughout, and adapted to substantially prevent blood intrusion into said semipermeable membrane.

12. The electrotransport device of claim 1, wherein said semipermeable membrane is configured to selectively allow the flow of ionized molecules therethrough.

13. The electrotransport device or claim 1, wherein said first electrode is configured as one of a solid, a suspension, a gel, and a solution.

14. The electrotransport devise of claim 1, wherein said second electrode is configured as one of a solid, a suspension, a gel, and a solution.

15. The electrotransport device of claim 1, wherein said first electrode and said beneficial agent are substantially interspersed throughout at least a portion of said compartment.

16. The electrotransport device of claim 1, further comprising a second semipermeable membrane disposed adjacently under at least a portion of second electrode, said second semipermeable membrane configured to be in fluid communication with a second beneficial agent contained in said second electrode, said second semipermeable membrane adapted to be implanted under at least a portion of a subject's stratum corneum in whom the electrotransport device has been implanted.

17. The electrotransport device of claim 1, wherein said first ad second electrode are configured as part of a unitary housing.

18. The electrotransport device of claim 1, wherein at least a portion of said semipermeable membrane comprises a material configured to be resorbable by a subject's body tissues in whom the electrotransport device has been implanted.

19. An electrotransport device for delivering molecules of a beneficial agent to tissue of a subject upon implantation, said electrotransport device comprising:
   a plurality of spaced apart electrodes, each of said plurality of spaced apart electrodes adapted to be placed over a subject's tissue surface;
   wherein at least one of said plurality of spaced apart electrodes comprises an electropositive or an electronegative material;
   at least one insulated conductor extending between two of said plurality of spaced apart electrodes;
   at least one reservoir disposed under an electrically conducting area of a first electrode of said plurality of spaced apart electrodes, said at least one reservoir adapted to accommodate the molecules of beneficial agent; and
   a bio-compatible ion exchange membrane configured to conduct a current disposed adjacently under said at least one reservoir, said ion exchange membrane adapted to be implanted under at least a portion of the tissue of a subject;
   wherein a subject's stratum corneum tissue completes a circuit between said plurality of spaced apart electrodes upon implantation under the subject's skin surface and enables delivery of molecules of the beneficial agent to the subject.

20. The electrotransport devise of claim 19, wherein a pair of said electrodes are positioned a fixed distance from each other.

21. The electrotransport device of claim 19, wherein said semipermeable membrane is configured to allow the flow of the molecules therethrough responsive to delivery of an electric current thereupon.

22. The electrotransport device of claim 19, wherein said semipermeable membrane is configured to substantially inhibit transport or the molecules in the absence of an electric current delivered to one of the molecules and said semipermeable membrane.

23. The electrotransport device of claim 19, wherein said semipermeable membrane is configured to substantially inhibit transport of the molecules in the absence of an electric current.

24. The electrotransport device of claim 19, wherein said semipermeable membrane is configured to selectively allow the flow of ionized molecules therethrough.

25. The electrotransport device of claim 19, wherein at least part of said semipermeable membrane comprises a material configured to be resorbable by the subject's body tissues.

26. The electrotransport device of claim 19, further comprising a second semipermeable membrane disposed in current conducting relationship under a second electrode of said plurality of mutually spaced apart electrodes, said second semipermeable membrane adapted to be implanted under at least a portion of the subject's stratum corneum.

27. The electrotransport device of claim 19, further comprising a power source in electrical communication with said plurality spaced apart electrodes.

28. A method of electrically facilitating the transport of a beneficial agent to a body tissue of a subject, said method comprising:
   providing a plurality of electrodes configured to conduct electrical current in relation to said body tissue, a first electrode comprising electropositive material and a second electrode comprising electronegative material, said first and second electrodes configured on a single housing;
   providing at least one beneficial agent reservoir disposed adjacently to an electrically conductive area of at least one said plurality of electrodes;
   including a beneficial agent in said beneficial agent reservoir, providing at least one semipermeable membrane in fluid communication with said at least one beneficial agent reservoir, said at least one semipermeable membrane configured to substantially inhibit passive diffusion of a beneficial agent therethrough in the absence of an electrical current applied at said at least one semipermeable membrane and said beneficial agent;

implanting at least a portion of said at least one semipermeable membrane beneath a subject's stratum corneum skin layer, wherein, responsive to said implanting, a circuit is completed between said plurality of electrodes capable of transmitting a voltage from said plurality of electrodes and said at least one semipermeable membrane to said body tissues beneath said stratum corneum skin layer, said voltage effecting transport of said beneficial agent through said at least one semipermeable membrane, said voltage facilitating transport of said beneficial agent through said body tissue, and delivering said beneficial agent to the subject's body tissues.

29. The method according to claim 28, further comprising implanting the electrodes and the membrane in their entirety beneath the subject's stratum corneum skin layer.

30. The method according to claim 28, wherein said providing at least one semipermeable membrane comprises providing at least one semipermeable membrane configured as one of a cationic exchange membrane and an ionic exchange membrane.

31. The method according to claim 28, wherein delivering said beneficial agent to the subject comprises diffusing said beneficial agent through micropores of said at least one semipermeable membrane.

32. The method according to claim 28, wherein said at least one semipermeable membrane is configured to have a molecular cutoff adapted to substantially prevent blood intrusion into said at least one semipermeable membrane.

33. The method according to claim 28, wherein delivering said beneficial agent to said subject comprises electrostatically repelling said beneficial agent trough said at least one semipermeable membrane.

34. The method according to claim 28, further comprising implanting said electrodes and said beneficial agent reservoir under a skin surface of said subject.

35. The method according to claim 28, wherein said implanting at least a portion of said at least one semipermeable membrane beneath a stratum corneum skin layer comprises implanting a bottom-most surface of said at least one semipermeable membrane to a depth approximating about 20-100 μm below the stratum skin layer.

36. An intraocular delivery device for delivering a beneficial agent to a subject's eye using liquid present on the surface of the subject's conjunctiva to complete a circuit between two complementary electrodes configured within said intraocular drug delivery device, said intraocular drug delivery device comprising:

a membrane comprising a polymer, semipermeable to water, and further comprising first and second surfaces, said first surface being adapted to be placed on the subject's conjunctiva to interact with any liquid present thereon, said second surface configured to contain a beneficial agent for delivery to the subject;

a first electrode in fluid communication with said membrane and said beneficial agent, said first electrode comprising an electropositive or an electronegative material; and a second electrode comprising an electropositive or an electronegative material, said second electrode configured to be in fluid communication with the subject's conjunctiva, but, except for conductive material connecting said first and second electrodes, electrically isolated from said first electrode, said first and second electrodes being selected, when configured together as a circuit, to form a battery, said first and second electrodes configured on a unitary housing;

wherein, when said intraocular drug delivery device is placed on the subject's conjunctiva, any electrically conductive liquid present thereon completes an ionic circuit between said first and second electrodes;

wherein said electropositive or electronegative material of said first electrode is complementary to said second electronegative or electropositive material of said second electrode, respectively, such that when electrically connected with any electrically conductive liquid present on the subject's conjunctiva, said battery is formed that drives the beneficial agent through said membrane for delivery to the subject's conjunctiva upon completing an electronic circuit.

37. The intraocular delivery device of claim 36, wherein the electropositive or electronegative material of the first electrode is magnesium.

38. The intraocular device of claim 36, wherein the electropositive or electronegative material of the second electrode is carbon.

* * * * *

UNITED STATES PATENT AND TRADEMARK OFFICE
CERTIFICATE OF CORRECTION

PATENT NO. : 7,349,733 B2 Page 1 of 1
APPLICATION NO. : 10/003853
DATED : March 25, 2008
INVENTOR(S) : Ashok V. Joshi It is certified that error appears in the above-identified patent and that said Letters Patent is hereby corrected as shown below:

Title Page, (73), Assignee: should read as follows:
--Ceramatec, Inc.--.

Signed and Sealed this

Thirteenth Day of July, 2010

David J. Kappos
*Director of the United States Patent and Trademark Office*